US011576801B2

(12) United States Patent
Cutler

(10) Patent No.: US 11,576,801 B2
(45) Date of Patent: Feb. 14, 2023

(54) TOPICAL TREATMENT FOR ANORECTAL DISORDERS WITH AND WITHOUT SEAT CUSHION

(71) Applicant: Robert S. Cutler, Tequesta, FL (US)

(72) Inventor: Robert S. Cutler, Tequesta, FL (US)

( * ) Notice: Subject to any disclaimer, the term of this patent is extended or adjusted under 35 U.S.C. 154(b) by 284 days.

(21) Appl. No.: 16/750,372

(22) Filed: Jan. 23, 2020

(65) Prior Publication Data
US 2020/0237544 A1 Jul. 30, 2020

Related U.S. Application Data

(60) Provisional application No. 62/796,194, filed on Jan. 24, 2019.

(51) Int. Cl.
*A61F 5/00* (2006.01)
*A61K 9/00* (2006.01)
*A47C 7/74* (2006.01)
*A47C 7/18* (2006.01)

(52) U.S. Cl.
CPC .............. *A61F 5/0093* (2013.01); *A47C 7/18* (2013.01); *A47C 7/74* (2013.01); *A61K 9/0014* (2013.01)

(58) Field of Classification Search
CPC ......... A61F 5/0093; A47C 7/18; A47C 7/029; A47C 7/021; A47C 7/74; A61K 9/0014; A61K 9/0031
USPC ............... 297/452.26, 452.23, 452.21; 5/653
See application file for complete search history.

(56) References Cited

U.S. PATENT DOCUMENTS

| 3,359,577 | A | * | 12/1967 | Rogers | A47C 20/027 5/652 |
|---|---|---|---|---|---|
| D276,938 | S | * | 12/1984 | Pedersen | 5/636 |
| D279,642 | S | * | 7/1985 | Ross | D6/601 |
| D289,481 | S | * | 4/1987 | Reddick | D6/601 |
| 4,761,843 | A | * | 8/1988 | Jay | A47C 7/029 128/98.1 |
| 4,805,603 | A | * | 2/1989 | Cumberland | A61H 1/0218 128/DIG. 20 |
| 4,858,259 | A | | 8/1989 | Simmons et al. | |
| 5,409,500 | A | | 4/1995 | Dyrek | |
| 5,545,199 | A | | 8/1996 | Hudson | |
| 5,626,387 | A | * | 5/1997 | Yeh | B60N 2/58 297/180.12 |
| 5,800,491 | A | | 9/1998 | Kolen et al. | |
| 5,895,656 | A | | 4/1999 | Hirshowitz et al. | |
| 5,916,088 | A | | 6/1999 | Gueli | |
| 5,948,013 | A | | 9/1999 | Swezey et al. | |
| 6,009,578 | A | | 1/2000 | Davis | |
| 6,132,455 | A | | 10/2000 | Shang | |
| D444,980 | S | * | 7/2001 | Mowat | 5/636 |
| 6,409,748 | B1 | | 6/2002 | DeCarlo et al. | |
| 6,546,578 | B1 | * | 4/2003 | Steinmeier | B60N 2/7035 5/724 |
| 6,645,235 | B1 | | 11/2003 | Blackwell | |

(Continued)

FOREIGN PATENT DOCUMENTS

DE 102005026107 A1 * 12/2006 ............. A47C 7/022

*Primary Examiner* — Milton Nelson, Jr.
(74) *Attorney, Agent, or Firm* — Dunlap Bennett & Ludwig, PLLC

(57) ABSTRACT

A topical treatment for anorectal disorders with and without utilization of a contoured seat cushion with a temperature-adapted or electrical stimulation element that can provide hot or cold temperatures or electrical stimulation to the anorectal region.

5 Claims, 4 Drawing Sheets

(56) References Cited

U.S. PATENT DOCUMENTS

| | | | |
|---|---|---|---|
| 6,704,957 B2 * | 3/2004 | Rhodes | A61B 5/055 |
| | | | 5/639 |
| 7,022,335 B2 | 4/2006 | Hori et al. | |
| 7,272,936 B2 | 9/2007 | Feher | |
| 7,273,887 B1 | 9/2007 | Wepfer | |
| 7,331,184 B2 | 2/2008 | Lee | |
| D634,961 S * | 3/2011 | Lowery | D6/601 |
| 8,556,337 B1 | 10/2013 | Cornitius-Cary | |
| D695,365 S * | 12/2013 | Ban | D21/687 |
| D716,072 S * | 10/2014 | Rose | D6/601 |
| 9,545,391 B2 | 1/2017 | Rosenblum et al. | |
| 9,549,617 B1 | 1/2017 | Deluca | |
| D808,194 S * | 1/2018 | Wyborn | D6/601 |
| 10,791,845 B2 * | 10/2020 | Tacon | A47C 20/027 |
| 2003/0032996 A1 | 2/2003 | Hallman | |
| 2003/0035850 A1 | 2/2003 | Blanco | |
| 2006/0275218 A1 | 12/2006 | Tamarkin et al. | |
| 2007/0148105 A1 | 6/2007 | Spector | |
| 2008/0003273 A1 | 1/2008 | Feldkamp et al. | |
| 2008/0136231 A1 | 6/2008 | Doherty | |
| 2009/0169652 A1 | 7/2009 | Osborne | |
| 2009/0196840 A1 | 8/2009 | Lorenzo | |
| 2010/0055185 A1 | 3/2010 | Agisim et al. | |
| 2010/0237082 A1 | 9/2010 | Fernandez | |
| 2012/0040019 A1 | 2/2012 | Rosenblum et al. | |
| 2012/0053546 A1 | 3/2012 | Fogg et al. | |
| 2013/0066408 A1 | 3/2013 | Peardon | |
| 2013/0090710 A1 | 4/2013 | Rimoli | |
| 2014/0008945 A1 | 1/2014 | Widmann | |
| 2015/0040324 A1 | 2/2015 | Dungan | |
| 2015/0257554 A1 | 9/2015 | Ross et al. | |
| 2016/0066716 A1 | 3/2016 | Rao | |
| 2017/0128392 A1 * | 5/2017 | Maurello | A61K 36/87 |
| 2020/0231285 A1 * | 7/2020 | Udriste | A47C 7/18 |

* cited by examiner

TOPICAL TREATMENT FOR ANORECTAL DISORDERS WITH AND WITHOUT SEAT CUSHION

CROSS-REFERENCE TO RELATED APPLICATION

This application claims the benefit of priority of U.S. provisional application No. 62/796,194, filed 24 Jan. 2019, the contents of which are herein incorporated by reference.

BACKGROUND OF THE INVENTION

The present invention relates to medical treatments for anorectal disorders and, more particularly, to a topical treatment for anorectal disorders with and without seat cushion; specifically, internal and externally applied topical products (ointments, creams, lotions, suppositories, gels, wipes, etc.) which aid in relieving or protecting from various symptoms of anorectal disease or disorders such as burning, itching, irritation, pain or mild inflammation of the skin or mucous membranes associated with various anorectal disorders which may include but not to be inclusive of internal and external hemorrhoids, anal fissures, proctitis, cryptitis and the method of using such topical treatments, as well as using a contoured seat cushion with a temperature adaptive insert gel or electrothermal heat pad insert.

Hemorrhoids are one of the most common causes of anorectal pathology. Subsequently, hemorrhoids are blamed for virtually any anorectal complaint by patients and medical professionals alike even though there are other distinct or contributing disorders such as anal fissures, proctitis, cryptitis, etc. Confusion often arises because the term "hemorrhoid" has been used to refer to both normal anatomical structures and pathological structures. In the context of this application, "hemorrhoids" refers to the pathological presentation of hemorrhoidal venous cushions.

Hemorrhoidal venous cushions are normal structures of the anorectum and are universally present unless a prior surgical intervention has taken place. Because of their rich vascular supply, highly sensitive location, and tendency to engorge and prolapse, they are common causes of anal pathology. Symptoms can range from mildly bothersome, such as itching with is referred to as pruritus, to quite concerning, such as rectal bleeding. While it is a common condition diagnosed in clinical practice, many patients are too embarrassed to ever seek treatment. Consequently, the true prevalence of pathologic hemorrhoids is not known.

Hemorrhoidal venous cushions are a normal part of the human anorectum and arise from subepithelial connective tissue within the anal canal. Present in utero, these cushions surround and support distal anastomoses between the superior rectal arteries and the superior, middle, and inferior rectal veins. They also contain a subepithelial smooth muscle layer, contributing to the bulk of the cushions. Normal hemorrhoidal tissue accounts for approximately 15-20% of resting anal pressure and provides important sensory information, enabling the differentiation between solid, liquid, and gas.

Most people anatomically possess three main cushions. Although classically described as lying in the right posterior (most common), right anterior, and left lateral positions, this combination is found in only 19% of patients. Hemorrhoids can be found at any position within the rectum.

Hemorrhoids are classified by their anatomic origin within the anal canal and by their position relative to the dentate line. The dentate line is between the simple columnar epithelium of the rectum and the stratified epithelium of the anal canal. Internal hemorrhoids develop above the dentate line from embryonic endoderm. They are covered by the simple columnar epithelium of anal mucosa and lack typical somatic sensory innervation. Therefore, people who have swollen or inflamed internal hemorrhoids in isolation without coexisting pathology do not contribute to the majority of people who suffer from anorectal pain as their primary symptom.

External hemorrhoids develop from ectoderm and arise distal to the dentate line. They are covered by stratified squamous epithelium and receive somatic sensory innervation from the inferior rectal nerve rendering them painful when irritated, painful, swollen or thrombosed.

Mixed hemorrhoids are confluent internal and external hemorrhoids. Internal hemorrhoids drain through the superior rectal vein into the portal system. External hemorrhoids drain through the inferior rectal vein into the inferior vena cava. Rich anastomoses exist between these two and the middle rectal vein, connecting the portal and systemic circulations. It is for this reason that symptomatic external hemorrhoids can never exist without internal hemorrhoids as a contributing factor.

Hemorrhoids usually are not dangerous or life threatening. Very rarely, a patient can have bleeding so severe, that severe anemia or death may occur. In some cases, hemorrhoidal symptoms simply go away within a few days. But in most cases, hemorrhoidal symptoms eventually return, often worse than they were previously. The most common symptom of internal hemorrhoids is bright red blood covering the stool, on toilet paper, or in the toilet bowl. However, an internal hemorrhoid may protrude through the anus outside the body, becoming irritated and painful. This is known as a protruding or prolapsing internal hemorrhoid. Sudden external swelling is typically caused by a break of the external blood vessels which can feel like a localized hardened marble-like area. This condition is known as a thrombosed external hemorrhoid. Long standing external hemorrhoids represent skin which has been stretched over time. It's a problem for some people since there is extra skin in the area which causes difficulty for proper hygiene.

In addition, excessive straining, rubbing, or cleaning around the anus may cause irritation with bleeding and/or itching, which may produce a vicious cycle of symptoms.

Anal tears (fissures) are one of the most common causes of anorectal pain at bowel movement, which can be quite severe and last for some time. Tears are often associated with repeated trauma, e.g., passage of a hard stool, but can also occur during bouts of diarrhea, childbirth, narrowing of the anal canal or ulceration of a hemorrhoid. If a tear does not heal, it becomes a fissure. The main reason tears do not heal and become fissures is due to inflammation from repeated trauma and coexisting contributing factors such as internal hemorrhoids. Therefore, fissures are usually caused by another issue which needs to be treated so the fissure itself will heal. Many times, the cause of the fissure will require a vasoconstrictor inserted internally above the fissure which will treat the underlying condition and allow the fissure to heal. In difficult cases, a physician prescribed vasodilator can be applied directly to the fissure to try and aid in healing by increasing blood flow directly to the fissure in conjunction with the aforementioned discussed vasoconstrictor.

A number of hemorrhoid treating products are available on the market today, but none are designed to provide enhanced effectiveness by targeting both internal and external disorders and by using any FDA approved active ingredient in combination with other ingredients which the FDA classifies as supplements to target specific contributing factors thereby enhancing the effectiveness of the treatment.

Prior art is very specific to include External Use Only and is limited to FDA approved concentrations of Lidocaine as well as Phenylephrine and restrict a supplement to include Vitis vinifera (Grape) skin extract, aloe Barbadensis leaf juice extract, or Vitamin E. Prior art also requires an additional ingredient and list various ingredients some of which are commonly used as formulation "inactive" ingredients. Other ingredients include additional anorectal FDA active ingredients and two additional supplements, Eucalyptus oil and Ylang-ylang oil. In fact, some prior art refers to their required supplemental additional ingredients (Vitis vinifera (Grape) skin extract, aloe Barbadensis leaf juice extract, or Vitamin E, Eucalyptus oil and Ylang-ylang oil) as "homeopathic" which is incorrect.

In summary, prior art specify ingredients that must be included:
 a. Lidocaine
 b. Phenylephrine
 c. Vitis vinifera (Grape) skin extract, aloe Barbadensis leaf juice extract, or Vitamin E
 d. at least one FDA approved astringent
 e. at least one FDA approved protective
 f. at least one topical carrier
 g. External Use Only And specify which may include the following additional supplements:
 a. Eucalyptus oil and Ylang-ylang oil And specify ingredients or applications which must NOT include:
 a. glycerin,
 b. internal application There is an obvious need for medicated topical treatments that work more efficiently and effectively to reduce and relieve anorectal symptoms as well as the cause of these symptoms. An example would be a product which not only shrinks the hemorrhoid but also delivers immediate relief to the pain and itching, and other symptoms often associated with this and other anorectal conditions. Additionally, more often than not, swelling causes inflammation which can significantly worsen the signs and symptoms as well as the condition itself. Muscle spasm has also been frequently associated with anorectal pain and discomfort causing more pain with bowel movements and even causing bowel motility issues. Other causes of inflammation not related to hemorrhoids include proctitis of unknown etiology, various microbial infestations and bowel disorders.

The present invention is directed to a medicated treatment that contains FDA directed active ingredients within one of five categories as specified by the FDA either alone or in combination (as directed by the FDA). The FDA ingredients are then combined with ingredients in which the FDA classifies as "supplements" in order to enhance the overall effectiveness of the embodiment. Application of this treatment is designed to effectively reduce signs and symptoms of many anorectal disorders more effectively than either the FDA active ingredients or the supplements alone.

The formulation of the present invention combines FDA approved therapies designed to treat specific signs and symptoms of anorectal disorders with supplements that specifically support and enhance the treatment of contributing factors.

The FDA specifies treatments for anorectal disorders to include either alone or in combination the following:
 a. Local Anesthetic active ingredients
 b. Protectant active ingredients
 c. Vasoconstrictor active ingredients
 d. Astringent active ingredients
 e. Analgesic, anesthetic and antipruritic active ingredients
 f. Keratolytic active ingredients The FDA also specifies signs, symptoms and disorders which can be treated and what effect can be achieved using the approved ingredients. These include but are not totally inclusive of the following:
 a. Discomfort (including itching, pain, soreness, burning and relief from skin irritations)
 b. Anorectal Disorders (including hemorrhoids and other disorders)
 c. Anorectal Inflammation
 d. Swelling
 e. Protects irritated areas, inflamed anorectal surfaces and perianal skin and abrasions
 f. Forms a protective coating over inflamed tissues to help prevent drying
 g. Provide a cooling sensation In sum, the present invention relates to enhancing FDA approved topical treatments of anorectal disorders which include one to five categories of active ingredients being used alone or in combination as dictated in the anorectal monograph (specific reference presented elsewhere). The topical treatment can be used alone or in combination with other hemorrhoid treating devices and/or medications.

The present invention relates to topical treatments of signs, symptoms of anorectal disorders and physiologic mechanisms causing or contributing to these factors. More specifically, the present invention relates to enhancing FDA approved topical treatments with supplements that specifically support and enhance the treatment of factors contributing or causing signs and symptoms of anorectal disorders and disease, some of which do not even have FDA approved treatments.

The most common factors FDA approved active ingredients are designed to treat include discomfort (including itching, pain, soreness, burning and relief from skin irritations), anorectal inflammation, swelling, abrasions and tears, and drying of inflamed tissues. Other factors causing anorectal signs and symptoms (such as proctospasm), do not have specific FDA monograph approved treatments. In fact, the FDA does not provide for any products which have the potential to help heal or reduce bleeding. Examples of supplements which can used to treat these factors include:

Horse Chestnut (vascular support and reduction of swelling)
Algae Extract (antiviral contributors to inflammation)
Calendula Extract (wound healing)
Chamomile (reduces inflammation)
Lysine (antiviral contributors to inflammation)
Ginseng Root (reduces spasm)
Pomegranate (astringent)
Gotu Kola (vascular support and reduction of swelling)
Argan Oil (antibacterial, anti-inflammatory and antioxidant action)
Camellia sinensis Tea Plant (astringent)
Coconut Oil (pain relieving)
Turmeric (anti-inflammatory)
Candelilla Wax (protective barrier)
Lavender Oil (calming reduction of irritation, wound healing)
Linseed Oil (calming reduction of irritation and inflammation)
Olive Oil (antimicrobial, moisturizing)
Macadamia Oil (wound healing, moisturizing)

Avocado Oil (reduction of inflammation, wound healing, moisturizing)

Patchouli Oil (calms, moisturizes, anti-inflammatory, wound healing)

Castor Seed Oil (calms, moisturizes, anti-microbial)

Rose Hip Oil (moisturizes, anti-inflammatory)

Hyaluronate (improves absorption by enhancing dispersion of ingredients)

Cramp Bark (reduces spasm)

The present invention differs from the prior art for the following reasons:

1. The present invention does not specify for the use of any specific anorectal FDA drug category
2. The present invention does not specify for a combination of anorectal FDA drug categories
3. The present invention does not restrict supplements to include *Vitis vinifera* (Grape) skin extract, aloe Barbadensis leaf juice extract, and/or Vitamin E, *Eucalyptus* oil and Ylang-ylang oil
4. The present invention does not restrict the use of Glycerin
5. The present invention does specify external use only The present invention does address some or all the factors contributing to signs and symptoms in accordance with the anorectal monograph through combining FDA approved active ingredients with appropriate supplements which have been found to be scientifically effective in exhibiting an effect to help treat the factors contributing to signs and symptoms in accordance with the anorectal monograph, the FDA approved active ingredient reads, in part, as follows:

FDA Part 346—Anorectal Drub Products for Over-the-Counter Human Use

Subpart B-Active Ingredients § 346.10 Local anesthetic active Ingredients. The active ingredient of the product consists of any of the following when used in the concentration or within the concentration range established for each ingredient: (a) Benzocaine 5 to 20 percent. (b) Benzyl alcohol 1 to 4 percent. (c) Dibucaine 0.25 to 1 percent. (d) Dibucaine hydrochloride 0.25 to 1 percent. (e) Dyclonine hydrochloride 0.5 to 1 percent. (f0 Lidocaine 2 to 5 percent. (g) Pramoxine hydrochloride 1 percent. (h) Tetracaine 0.5 to 1 percent. (i) Tetracaine hydrochloride 0.5 to 1 percent. § 346.12 Vasoconstrictor active Ingredients. The active ingredient of the product consists of any of the following when used in the concentration or within the concentration range established for each ingredient. (a) Ephedrine sulfate 0.1 to 1.25 percent. (b) Epinephrine 0.005 to 0.01 percent. (c) Epinephrine hydrochloride 0.005 to 0.01 percent. (d) Phenylephrine hydrochloride 0.25 percent. § 346.14 Protectant active Ingredients. (a) The following active ingredients may be used as the sole protectant active ingredient in a product if the ingredient as identified constitutes 50 percent or more by weight of the final product. In addition, the following active ingredients may be used in concentrations of less than 50 percent by weight only when used in combinations in accordance with § 346.22 (a), (b), or (n). (1) Aluminum hydroxide gel. (2) Cocoa butter. (3) Glycerin in a 20- to 45-percent (weight/weight) aqueous solution so that the final product contains not less than 10 and not more than 45 percent glycerin (weight/weight). Any. combination product containing glycerin must contain at least this minimum amount of glycerin. (4) Hard fat. (5) Kaolin. (6) Lanolin, (7) Mineral oil. (8) Petrolatum. (9) Topical starch. (10) White petrolatum. (b) The following active ingredients may not be used as a sole protectant ingredient but may be used in combination with one, two, or three other protectant active ingredients in accordance with § 346.22 (a), (b), (n), and (o) and with the following limitations: (1) Calamine not to exceed 25 percent by weight per dosage unit (based on the zinc oxide content of calamine). (2) Cod liver oil, provided that the product is labeled so that the amount of the product that is used in a 24-hour period represents a quantity that provides 10,000 U.S.P. units of vitamin A and 400 U.S.P. units of cholecalciferol. (3) Shark liver oil, provided that the product is labeled so that the amount of the product that is used in a 24-hour period represents a quantity that provides 10,000 U.S.P. units of vitamin A and 400 U.S.P. units of cholecalciferol. (4) Zinc oxide not to exceed 25 percent by weight per dosage unit. § 346.16 Analgesic, anesthetic, and antipruritic active Ingredients. The active ingredient of the product consists of any of the following when used within the concentration range established for each ingredient: (a) Camphor 0.1 to 3 percent. (b) Juniper tar 1 to 5 percent. (c) Menthol 0.1 to 1 percent. § 346.18 Astringent active Ingredients. The active ingredient of the product consists of any of the following when used within the concentration range established for each ingredient: (a) Calamine, within a concentration range of 5 to 25 percent by weight per dosage unit (based on the zinc oxide content of calamine). (b) *Hamamelis* water, "The National Formulary XI," 10 to 50 percent. (c) Zinc oxide, within a concentration range of 5 to 25 percent by weight per dosage unit. * 346.20 Keratolytic active Ingredients. The active ingredient of the product consists of any of the following when used within the concentration range established for each ingredient: (a) Alcloxa 0.2 to 2 percent. (b) Resorcinol 1 to 3 percent.

§ 346.22 Permitted combinations of anorectal active Ingredients. (a) Any two, three, or four protectants identified in (a) § 346.14 may be combined, except aluminum hydroxide gel in § 346.14(a)(1) and kaolin in § 340.14(a)(5) may not be combined with any ingredient in § 346.14(a) (2), (4), (6), (7), (8) and (10), and (b) (2) and (3), provided that the combined percentage by weight of all protectants in the combination is at least 50 percent of the Federal Register/ Vol. 55, No. 150/Friday, Aug. 3, 1990/Rules and Regulations final product (e.g., 1 gram of a 2-gram dosage unit). Any protectant ingredient included in the combination must be present at a level that contributes at least 12.5 percent by weight (e.g., 0.25 gram of a 2-gram dosage unit), except cod liver oil and shark liver oil. If an ingredient in 1 346.14(b) is included in the combination, it must not exceed the concentration limit specified in § 346.14(b). (b) Any single anorectal ingredient identified in § 348.10, 346.12, 346.16, 346.18, or 346.20 may be combined with up to four protectants in accordance with paragraph (a) of this section. (c) Any single local anesthetic identified in § 346.10 may be combined with any single vasoconstrictor identified in § 346.12. (d) Any single local anesthetic identified in 5 346.10 may be combined with any single astringent identified in § 346.18. (e) Any single local anesthetic identified in § 346.10 may be combined with any single keratolytic identified in 1 346.20. (f) Any single vasoconstrictor identified in § 346.12 may be combined with any single astringent identified in § 346.1. (g) Any single analgesic, anesthetic, and antipruritic Identified in § 346.16 may be combined with any single astringent identified in § 346.18. (h) Any single analgesic, anesthetic, and antipruritic identified in 1 346.16 may be combined with any single keratolytic identified in § 348.20. (1) Any single astringent identified in § 346.18 may be combined with any single keratolytic identified in § 346.20. 0) Any single local anesthetic identified in 1 346.10 may be combined with any single vasoconstrictor identified in § 346.12 and with any single astringent Identified in § 346.18. (k) Any single local anesthetic identified in § 346.10 may be combined with any single astringent Identified in § 346.18 and with any single keratolytic identified in § 346.20. (1) Any single vasoconstrictor identified in 1 346.12 may be combined with any single analgesic, anesthetic. and antipruritic identified in § 346.18 and with any single astringent identified in § 346.18. (in) Any single analgesic, anesthetic, and antipruritic identified in § 348.16 may be combined with any single astringent identified in 1 346.18 and with any single keratolytic identified in 9 346.20. (n) Any combination of ingredients listed in paragraphs (c) through (in) of this section may be combined with up to four protectants in accordance with paragraph (a) of this section. (o) Any product containing calamine for use as a protectant and/or as an astringent and/or containing zinc oxide for use as a protectant and/or as an astringent may not have a total weight of zinc oxide exceeding 25 percent by weight per dosage unit.

SUMMARY OF THE INVENTION

In one aspect of the present invention, a composition including: at least one U.S. Food & Drug Administration (FDA) approved anorectal active ingredient; and at least one supplement which exhibits an activity as defined under the following categories: exhibit activity against inflammation; exhibit activity against irritation contributing to discomfort and bleeding; exhibit a calming or soothing effect; designed to reduce muscle spasm; antimicrobials that are either a direct cause of inflammation or part of the inflammatory process; dispersion agents; wound healing supplements; pain relieving supplements; and supplements which provide vascular support.

In another aspect of the present invention, a cushioned seat for relieving tailbone and hemorrhoid pain including the following: a seat cushion dimensioned to accommodate a human sitter centered over a central section; an operative contoured surface provided along an upward-facing portion of the seat cushion, the operative contoured surface providing: a rear contour having a first elevation at both longitudinal edges and a rear edge; the first elevation being greater than other elevations of the rear contour; the rear contour slopes downward longitudinally until a transition area; both longitudinal edges sloping downward laterally toward each other and until a medial contour; the transition area sloping upwardly as it extends away from the rear contour to a lateral contour; the thing contour cresting at a second elevation and sloping downwardly to a forward contour; and the second elevation being greater than the first elevation, whereby the lateral contour raises a posterior thigh of the human sitter allowing associated buttocks and external hemorrhoids vessels to be in direct contact with the central section. In certain embodiments including a pocket disposed along the central section; and a temperature adapted element retained in the pocket, or wherein the temperature adapted element integrated to the central section.

These and other features, aspects and advantages of the present invention will become better understood with reference to the following drawings, description and claims.

DETAILED DESCRIPTION OF THE INVENTION

Figure 1:
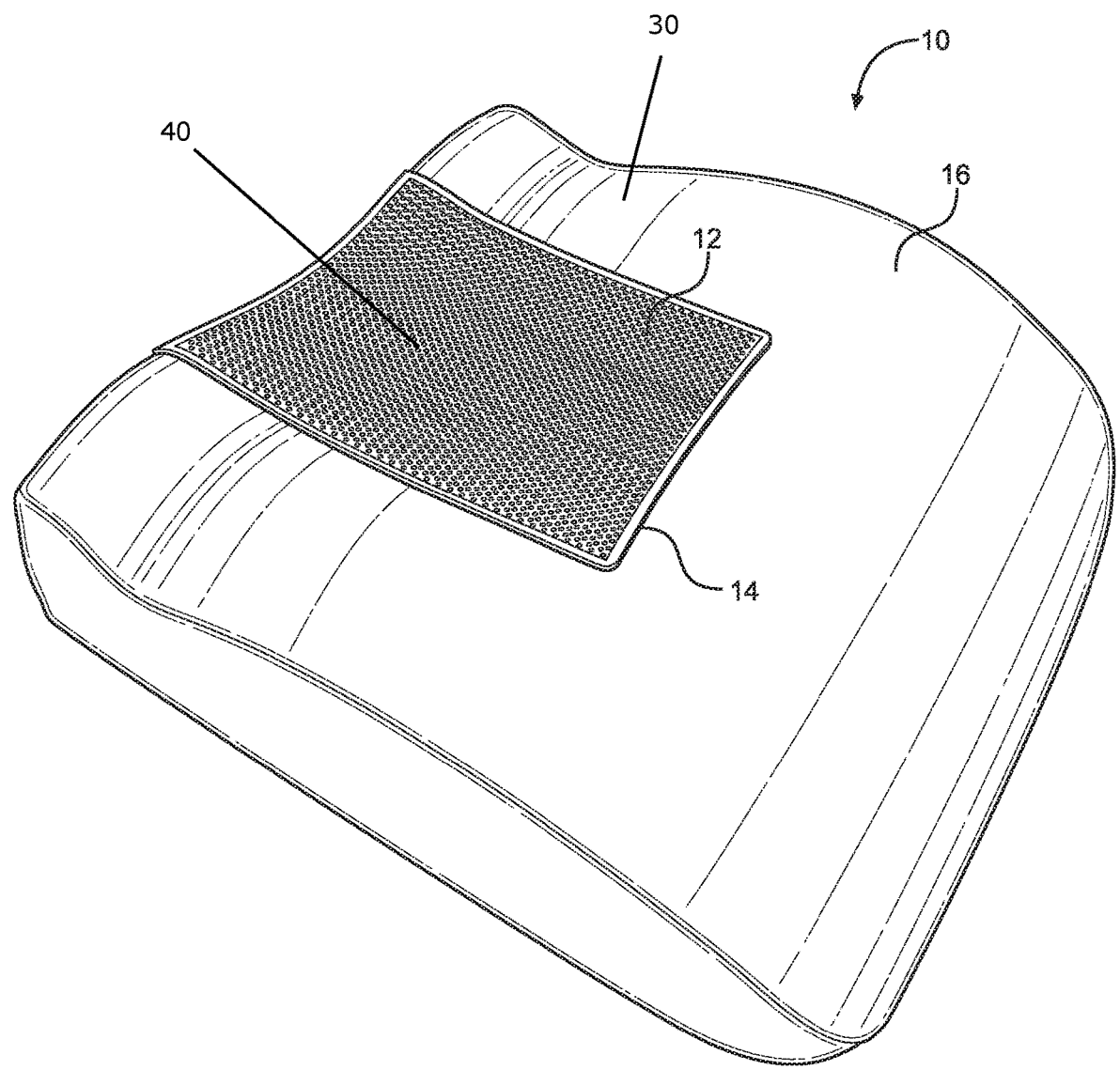
FIG. 1 is a perspective view of an exemplary embodiment of the present invention.

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

The present invention uses "supplements" to create "enhanced" effectiveness by treating pathophysiology from a multidisciplined approach. There are many causes of anorectal symptoms therefore our invention will specify at least one supplement from the various types of supplements that may be specified depending on the formulation. These may include supplements from one or in combination with any or all the following:
1. exhibit activity against inflammation
2. exhibit activity against irritation contributing to discomfort and bleeding
3. exhibit a calming or soothing effect
4. designed to reduce muscle spasm (which may be associated with pain or cause other types of disfunction or symptoms)
5. antimicrobials (which can be either a direct cause of inflammation or part of the inflammatory process)
6. dispersion agents (to help the treatment spread out over a greater surface area thereby increasing the dose dependent effectiveness and onset of action)
7. wound healing supplements
8. pain relieving supplements
9. supplements which provide vascular support (to aid in healing and reduction of swelling)

The present invention is described in the general context of compositions for treating hemorrhoids and conditions related to hemorrhoids as well. This includes but is not limited to anal fissures, piles, proctitis, proctospasm, abscesses, fistulas and related conditions. Additionally, such embodiments can be used to relieve or reduce pre- and post-surgical anorectal symptoms and potentially aid in healing (per scientific references on wound healing supplements if contained in one of the embodiments of the present invention).

As used herein, the term "treatment" refers to the medical management of a patient with the intent to cure, ameliorate, stabilize, or prevent a hemorrhoids and related conditions or disorders. This term includes active treatment, that is, treatment directed specifically toward the improvement of hemorrhoids and related conditions and includes palliative treatment, that is, treatment designed for the relief of symptoms rather than the curing of hemorrhoids and related conditions.

As used herein, the term "alleviate" or "alleviating" refers to lightening or lessening the severity of a symptom, condition, or outbreak of hemorrhoids and related conditions. For example, a treatment that reduces the severity of pain in a subject can be said to alleviate pain.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms associated with hemorrhoids and related conditions but is generally insufficient to cause adverse side-affects. The specific therapeutically effective dose level for any particular patient will depend upon a variety of factors including the severity of the hemorrhoids and related conditions; the specific composition employed; the age, body weight, general health, sex and diet of the patient; the duration of the treatment; drugs used in combination or coincidental with the specific compound employed and like factors well known in the medical arts.

For example, it is well within the skill of the art to start doses of a composition at levels lower than those required to achieve the desired therapeutic effect and to gradually increase the dosage or the amount of applications of the cream until the desired effect is achieved.

As used herein, the term "pharmaceutically acceptable carrier" refers to sterile aqueous or nonaqueous solutions, dispersions, suspensions or emulsions, for reconstitution into steriletopical ointments and/or creams. Examples of suitable aqueous and nonaqueous carriers, diluents, solvents or vehicles include water, ethanol, methanol, isopropanol, polyols (such as glycerol, propylene glycol, polyethylene glycol and the like), carboxymethylcellulose and suitable mixtures thereof, vegetable oils (such as olive oil, light mineral oil, cottonseed oil, castor oil, and the like) and injectable organic esters such as ethyl oleate. Proper fluidity can be maintained, for example, by the use of coating materials such as lecithin, by the maintenance of the required particle size in the case of dispersions and by the use of surfactants.

The term "pharmaceutically acceptable salt" refers to a salt prepared from a base or acid that is acceptable for administration to a patient, such as a mammal. Such salts can be derived from pharmaceutically acceptable inorganic or organic bases and from pharmaceutically acceptable inorganic or organic acids. Salts derived from pharmaceutically acceptable inorganic bases include aluminum, ammonium, calcium, copper, ferric, ferrous, lithium, magnesium, manganic, manganous, potassium, sodium, zinc and the like. Particularly preferred are ammonium, calcium, magnesium, potassium and sodium salts. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maple, malic, mandelic, methanesulfonic, mucic, naphthalenesulfonic, nicotinic, nitric, pamoic, pantothenic, phosphoric, succinic, sulfuric, tartaric (providing a tartrate or bitartrate), p-toluenesulfonic and the like. Particularly preferred are citric, hydrobromic, hydrochloric, maple, phosphoric, sulfuric and tartaric acids.

The terms "anorectal disease", "painful conditions of the anal region", "anal conditions", "anal pain", and the like, are used herein to describe symptoms of discomfort or pain in a person's anorectal area, or the diseases and disorders that produce them. Anorectal diseases include anal fissures, thrombosed or inflamed hemorrhoids, pain associated with the aftereffects of anal surgery and procedures (such as rubber-band ligation of internal hemorrhoids) and chronic anal pain. The anorectal area comprises the anal mucosa, the mucosa of the most distal portion of the rectum, the internal and external anal sphincters, the skin immediately surrounding the anus.

FDA Classification "Active agent" or "Active ingredient", as used herein, refers to any component in a composition of the present invention that has been approved for use in anorectal disorders by the FDA (and referenced in the anorectal monograph) because of their known ability to reduce the symptoms associated with anorectal disease.

"Supplements" differ from "active agent" or "Active ingredient", as used herein, to mean any component that can be added to a composition that has some biological effect according to a consensus of reference guides on supplements, whether the biological effect is directly related to anorectal disease or not. The biological effect is preferably curative. Such components might have analgesic or anesthetic effects, Such components might alternatively have an activity unrelated to pain reduction such as anti-inflammatory effect, muscle relaxing effects, vascular support effects, calming effects, improved dispersion, and anti-microbial effects as examples.

There are no standard concentrations provided for supplements by the FDA so none will be specified. Additionally, while the FDA does recognize the use of supplements with certain guidelines and provisions, the marketing of such claims are limited so that the inclusion of such ingredients may be listed as "inactive ingredients".

Xylocaine has the generic name lidocaine and may be used as an active ingredient of the composition of the present invention (other FDA approved anesthetics may also be used and are listed in the anorectal monograph). Lidocaine is an intermediate-duration anesthetic, that is incorporated into the gel, lotion, paste, wipe or solution of the present invention and can be safely applied within an effective dosage protocol topically usually every 3-4 hours to obtain relief of pain. If used, the FDA specified concentration ranges from as low as 2% to as high as 5%. Lidocaine is a local anesthetic and antiarrhythmic drug. Lidocaine is used topically to relieve itching, burning and pain from skin inflammations that is often associated with hemorrhoids and related conditions. Together with phenylephrine HCl (which is one example of an FDA approved vasoconstrictor), these two ingredients work to shrink and relieve pain and itching associated with hemorrhoids and related conditions almost immediately. The topical treatment of the present invention may consist of a single application of a treatment containing concentrations of phenylephrine HCl and lidocaine permitted by the Food and Drug Administration (FDA) in combination with a supplement which is sufficient for some outbreaks of an anorectal condition but most cases require multiple applications.

The compositions of the present invention can also contain adjuvants such as preservatives, wetting agents, emulsifying agents and dispersing agents. Prevention of the action of microorganism contamination can be ensured by the inclusion of various antibacterial and antifungal agents such as glycerin, capryl hydroxamic acid, paraben, chlorobutanol, phenol, sorbic acid, chlorohexidine digluconate, and the like. Antioxidants, such as BHT, can be included. It can also be desirable to include isotonic agents such as sugars, sodium chloride and the like.

The inventor contemplates that any conventional adjuvants can be used in the present composition. These may include antioxidants, for example sodium or potassium metabisulfite; isotonic agents such as sodium chloride;

chelating agents such as EDTA or citric acid; pH adjustment agents such HCl or NaOH, present in an amount desirable to achieve a pH of, for example, from 3.3-5.5; minor impurities such as aluminum salts; and other ingredients. Other adjuvants that may find use herein include opiates, such as morphine and fentanyl (used to provide epidural/spinal anesthesia); NMDA antagonists, such as dextromethorphan; clonidine; antiinflammatory agents; antibiotics; and the like. When preparing the pharmaceutical compositions of this invention, the active ingredient is customarily diluted by an excipient. Representative examples of suitable excipients include water, sterile saline, syrup, and methylcellulose. The formulations can additionally include emulsifying and suspending agents; preserving agents, such as methyl- and propylhydroxy-benzoates; and flavoring and coloring agents.

The compounds of this invention may be formulated using conventional techniques such as those described in Remington's Pharmaceutical Sciences, Mace Publishing Co., Philadelphia, Pa. 17th Ed. (1985) and "Modern Pharmaceutics," Marcel Dekker, Inc. 3.sup.rd Ed. (G. S. Banker & C. T. Rhodes, Eds.). Pharmaceutically acceptable salts of the active agents (e.g., acid addition salts) may be prepared using standard procedures known to those skilled in the art of synthetic organic chemistry and described, e.g., by J. March, Advanced Organic Chemistry: Reactions, Mechanisms and Structure, 4th Ed. (New York: Wiley-Interscience, 1992).

In one embodiment of the present invention, the composition designed to treat hemorrhoids and related conditions comprises what the FDA recognizes as a therapeutic effective amount of phenylephrine HCl (or other FDA approved vasoconstrictor) for relieving swelling caused by hemorrhoids and related conditions. Phenylephrine HCl is an active ingredient of the ointment that acts to shrink the swollen tissues associated with hemorrhoids by constricting blood vessels that feed blood and fluid to the area around the hemorrhoid. Phenylephrine HCl is a α-adrenergic receptor agonist that binds to α-adrenergic receptors that once activated set off a physiological process in the body that restricts blood supply to the area of the hemorrhoids and thereby reduces swelling in this area. Although very effective, the favorable effects of phenylephrine HCl on hemorrhoids are often masked by the itching and pain in the area around the hemorrhoid(s). To relieve this pain the present invention may also include lidocaine, or any other FDA monograph approved analgesic, anesthetic, antipruritic or astringent ingredient.

To enhance the effects of the topical treatment of the present invention, without adding more than the FDA approved amounts of the active ingredients discussed above, supplements are added to the topical treatment. These supplements can be used alone, in combination with other supplements which exhibit similar characteristics, or with supplements which exhibit different characteristics many of which can be described below. Examples of references supporting the use of supplements for these indications include:
1. Culpeper's Complete Herbal: Over 400 Herbs and Their Uses Arcturus Publishing Limited Jan. 30, 2012
2. The Herb Society of America
   Encyclopedia of Herbs & Their Uses
   By Deni Bown
   Dorling Kindersley Publishing Inc. 1995
3. https://examine.com/
4. Encyclopedia of Dietary Supplements Second Edition Informa Healthcare, 52 Vanderbilt Avenue, 7th floor, New York, N.Y. 10017, USA 2010

Examples of the most desirable characteristics of the supplements being used consist of the following list which is not all-inclusive:
1. exhibit activity against inflammation
2. exhibit activity against irritation contributing to discomfort and bleeding
3. exhibit a calming or soothing effect.
4. designed to reduce muscle spasm (which can be associated with pain)
5. antimicrobials (which can be either a direct cause of inflammation or part of the inflammatory process)
6. dispersion agents (to help the treatment spread out over a greater surface area thereby increasing the dose dependent effectiveness and onset of action)
7. wound healing supplements
8. pain relieving supplements
9. supplements which provide vascular support.

These supplements can be safely used in combination with phenylephrine HCl and lidocaine or any other FDA approved anorectal active ingredient to enhance the potency and extend the period of effectiveness of the topical treatment of the present invention. Examples of the effects these supplements can exhibit is further described below.

*Camellia sinensis* [also known as tea tree] as an example is—rich in flavonoids including anthocyanins, oligomeric proanthocyanidins (OPCs), quercetin and isoquercitrin and have astringent and other properties. Clinical trials have proven the efficacy of preparations made from many supplements such as horse chestnut and Gotu Cola as examples in the treatment of venous insufficiency. These effects have been in reducing significantly lower leg edema and circumference whilst improving other chronic symptoms to a clinically relevant extent. This relates to increased pressure typically found in hemorrhoid disease in which such reduction of pressure can effectively reduce or resolve prolapsing or protruding hemorrhoids.

As stated above, *Camellia sinensis* contain a wide range of polyphenol flavonoids including flavon (op-glycosides and glucuronides, quercetin-3-O-beta-D-glucuronide (main flavonoid), isoquercitrin, anthocyanins, oligomeric proanthocyanidins, catechin, epicatechin monomers and dimers; gallic acid and astilbine. Turmeric as another example reduces swelling and compliments the active ingredient phenylephrine HCl. The proposed mechanism of action by which Turmeric (curcumin) induces its anti-inflammatory effects is yet to be fully elucidated. Studies have shown that peroxisome proliferator-activated receptor gamma (PPAR-γ) has been associated with anti-inflammatory effects. PPARs belong to the superfamily of nuclear receptors consisting of three genes that give rise to three different subtypes, PPAR-α, PPAR-δ, and PPAR-γ. Among them, PPAR-γ is the most widely studied form. Upon ligand binding, PPAR-γ forms heterodimers with the retinoid X receptor and binds to a peroxisome proliferation response element (PPRE) in a gene promoter leading to regulation of gene transcription. In that regard, we have recently shown that gene and protein levels of PPAR-γ in the liver decreased by approximately 50% at 20 hours after the onset of sepsis. Pretreatment with curcumin for 3 days at 0.24 μmol/kg body weight in these septic rats produced 45% and 65% increase in PPAR-γ mRNA and protein levels, respectively.

Since they have a different mode of physiological operation than phenylephrine HCl they last for a longer period of time than phenylephrine HCl thereby extending the effectiveness of the topical treatment of the present invention.

In addition to these ingredients, the topical treatment of the present invention may also include Lavender Oil. which is another example of a supplemental ingredient that complements the active ingredients of the present invention. This is effective in further reducing inching and soothing the area around the hemorrhoid(s). Punica granatum is an astringent that helps to heal open wounds and therefore aids in reducing bleeding and itching often associated with hemorrhoids and related conditions.

The topical treatment of the present invention combines both conventional medical compositions such as phenylephrine HCl and lidocaine with supplemental compositions such as horse chestnut, chamomile, etc. to produce a topical treatment that is more potent for treating hemorrhoids and related conditions than other topical treatments that use conventional ingredient or supplemental ingredients alone. In certain embodiments, such treatments may provide effects which are not able to be achieved using traditional FDA approved active ingredients. In addition, the overlapping of ingredients that has cumulative and complementary affects aids in prolonging the therapeutic effects of the claimed topical treatment as compared to other topical treatments for treating anorectal disorders available on the market today. That is, the claimed topical treatment enhances this by adding additional ingredients beyond what the FDA provides for and considers "active" in the anorectal monograph. These supplemental ingredients enhance the potency of the claimed topical treatment as well as extend the duration of effectiveness.

The compositions of the present invention are typically administered in a therapeutically effective amount. It will be understood, however, that the amount of the compound administered will be determined by the FDA dosing recommendations governing the active drug ingredients.

In one preferred embodiment, the treatment comprises 4% to 5% by weight of lidocaine and 0.25% by weight of phenylephrine HCl as active ingredients and algae extract, chamomile, *Ginseng*, and Sodium Hyaluronate as supplemental ingredients. The topical treatment may also be comprised of additional or different active ingredients as well as different supplemental ingredients and combined with non-active components including benzyl alcohol, carbomer, cholesterol, hydrogenated lecithin, isopropyl myristate glycol, triethanolamine, Vitamin E Acetate, and purified water, fragrances, coloring agents, vitamins, oils, stability agents and/or other ingredients necessary to maintain the effectiveness of the topical treatment.

The carbomer polymers of the ointment are used as thickening, dispersing, and emulsifying agents. They are also used to control the release of medicaments from time-release tablets or from entrapped systems. Carbomers are largely insoluble in water and in the majority of common solvents. When neutralized (with bases, e.g., hydroxides or amines), Carbomers can be soluble in water, alcohol and glycerin. Carbomers are hygroscopic in nature, swelling to many times their original volume when in contact with a solvent. Such swollen particles remain discrete in various mucilaginous or colloidal dispersions. Although swelling is inherently caused by their hydrophilic nature, "maximum volume swell" does not typically occur in water until the polymers are converted to partial organic or inorganic salts. The increased volume is generally stable at all pH levels but increases as neutralization increases. Maximum volume occurs at 50-90% neutralization, with a neutralization of 75% normally occurring at pH 7.0.

The topical treatment composition of the present invention is made by mixing the active ingredients and supplemental ingredients into a pharmaceutically acceptable carrier and adding the other ingredients as well as water in an order that provides a topical cream, ointment, lotion, gel, spray, suppository, wipe etc. wherein the activity of the conventional and supplemental ingredients are maintained. Conventional producing procedures used in the art can also be used to make the desired composition of the present invention.

For example one method that can be used to produce the water-based topical ointment of the present invention includes the steps of: providing a mixture of aqueous solvent, one or more penetration enhancers, and, optionally, one or more preservatives; adding to the mixture one or more thickeners; adding to the mixture one or more emulsifiers; heating the mixture to at least a temperature sufficient to solubilize or melt the one or more thickeners and/or one or more emulsifiers; adding phenylephrine HCL and lidocaine as well as the supplemental ingredients; and adjusting the pH of the mixture to from about 4 to about 6 with a pH-adjuster.

In a further aspect, the pH is adjusted before or during one or more of the providing, adding, and heating steps. In a yet further aspect, the pH is adjusted after the providing, adding, and heating steps. In one aspect, the ointment comprises at least about 60% aqueous solvent by weight. Typically, the mixture is provided as a uniform suspension (dispersion) of ingredients. In certain aspects, the mixture can appear as an emulsion or a solution. It is understood that this method is just one method that can be used to make the ointment of the present invention but other methods available in the art can also be used.

Once the topical treatment composition is produced it can be provided in a single dosage convenient packaging, a squeezable tube, a wide-mouth jar, saturated on a pad for application, suppository sheet, or any other suitable storage means.

As dictated elsewhere it is understood that the compositions of the disclosed invention can be provided in a form suitable for topical use such as, for example, cream, ointment, lotion, gels and the like. Further, the compositions can be in a form suitable for use in transdermal devices as well such as wipes, clothes, applicators, pads, and other applications including specifically designed under garments that are designed to keep the ointment in place. All these formulations can be prepared via conventional processing methods as discussed above.

In addition, although anorectal disorders are explicitly discussed throughout the application it is understood that the composition can be used with many specific anal conditions including but not limited to hemorrhoids, anal fissures, anal tears, anal scarring and the like.

Finally, it is understood that the topical treatment of the present invention can be included as part of a kit that contains a hemorrhoid reducing/comfort seat as well as instructions for using the seat and applying the topical treatment thereafter.

The present invention includes a specialized foam comfort cushion with a mesh pocket to hold a cold or hot gel insert or electric heating pad. This cushion can be sat on comfortably and the gel insert will provide direct cold or heat as desired to the external hemorrhoidal cushions. Cold therapy has been found to reduce inflammation, swelling and soreness. Cold is typically recommended as an anti-inflammatory during the first 24 hours of injury as an example in the case of a ruptured external hemorrhoid blood vessel causing an external thrombotic hemorrhoid. Heat therapy can help relieve discomfort by providing a warm, comforting sensation, Heat also helps increase blood flow throughout the body, Increased blood flow can heal injuries faster. In the case of a thrombosed external hemorrhoid as an example, heat is advised after 24 hours to improve vascular circulation thereby allowing improved blood flow and drainage thereby allowing reabsorption of the clot(s).

Therefore, the present invention is also directed to the method of treating hemorrhoids and related conditions by applying the topical treatment of the present invention either alone or in combination with the use of a cushion device designed to provide comfort while applying heat or cold directly to the perianal location so as to alleviate discomfort, reduce swelling, improve healing or as an example, cause an external thrombosis to be reabsorbed by the body. This does not eliminate the itching and swelling often associated with this condition; however, the topical treatment of the present invention is designed to reduce these symptoms as discussed above.

Figure 2:
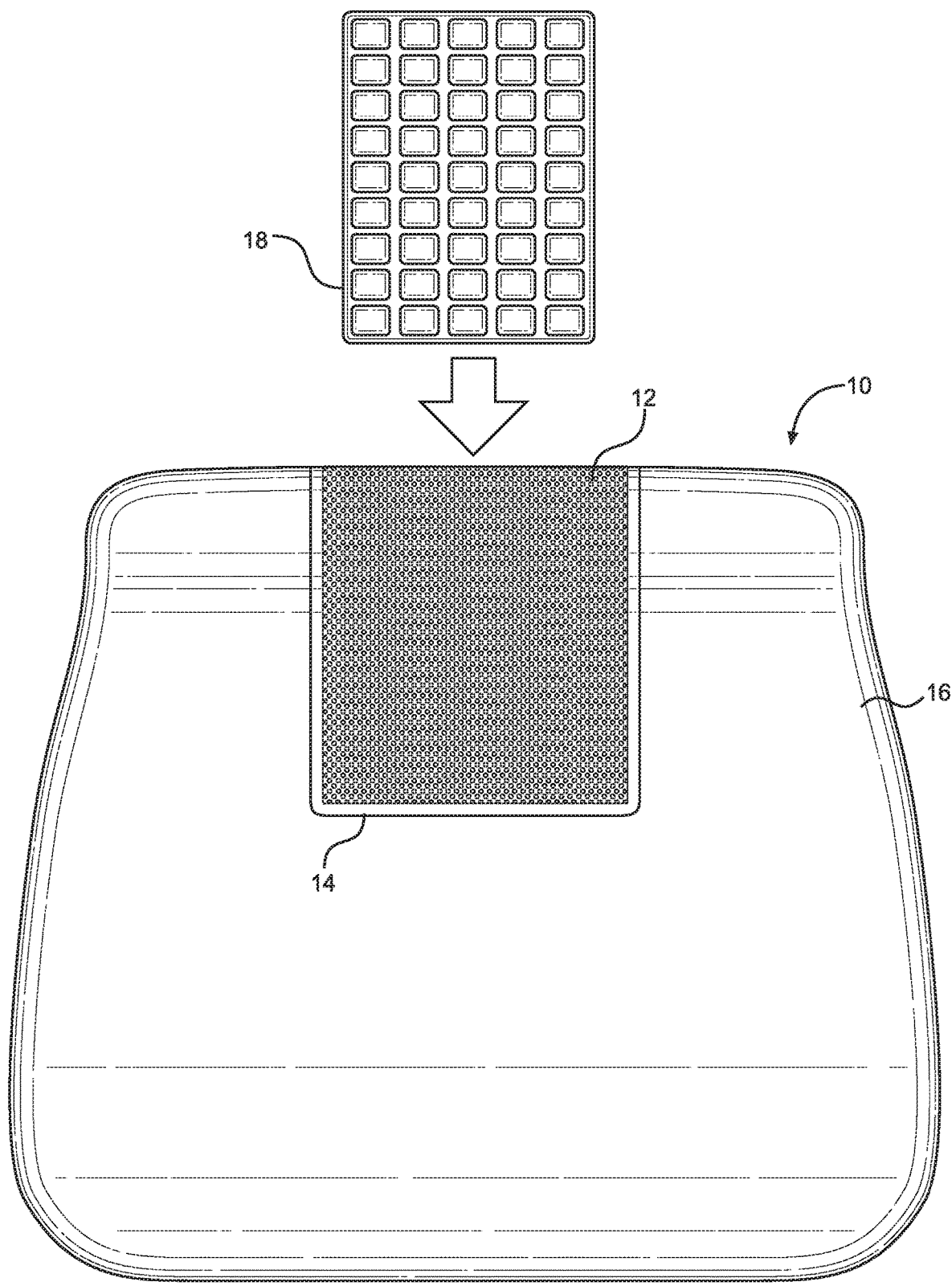
FIG. 2 is a top view of an exemplary embodiment of the present invention, demonstrating use of a cooling pack.
Figure 3:
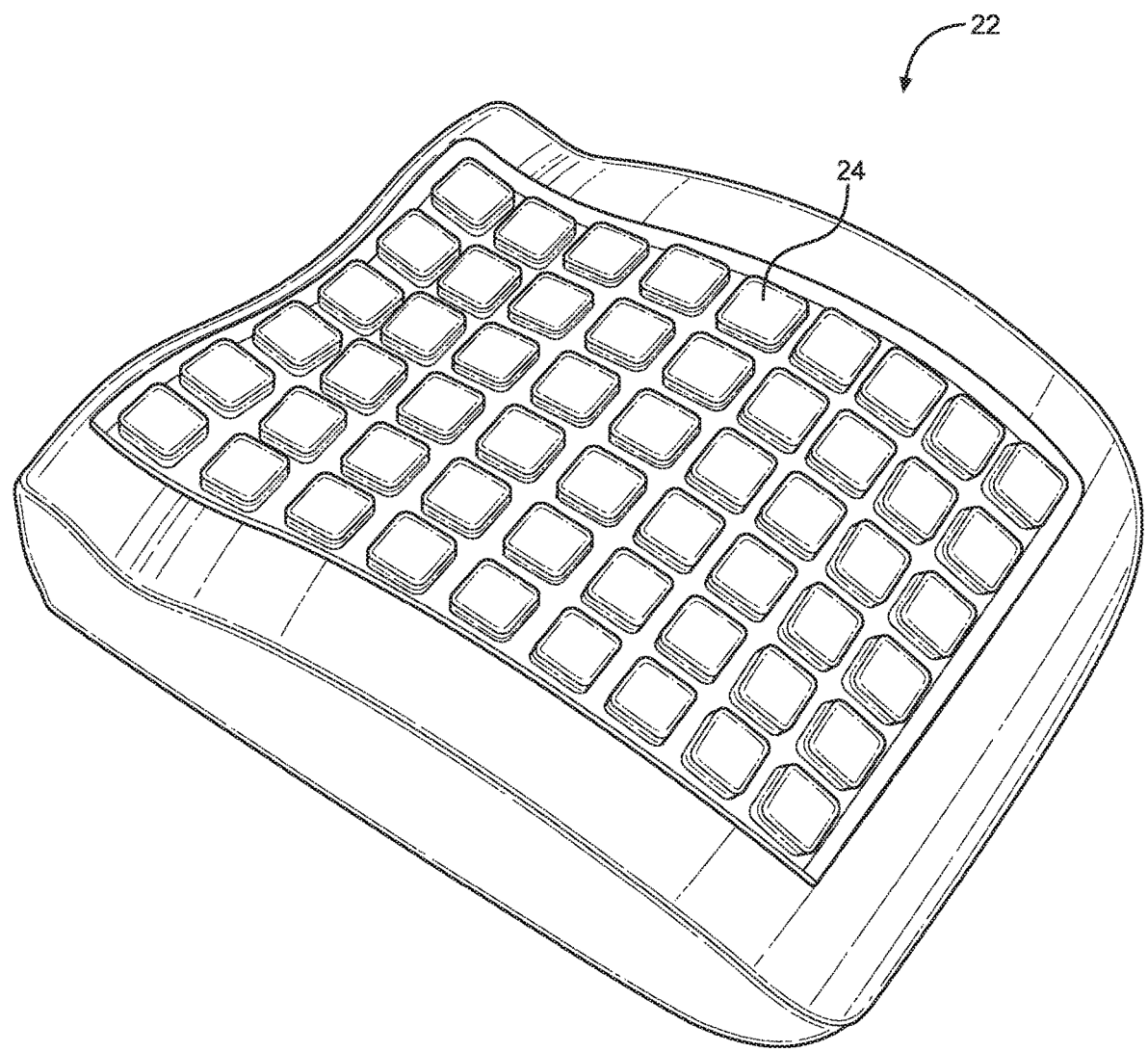
FIG. 3 is a perspective view of an exemplary embodiment of the present invention.
Figure 4:
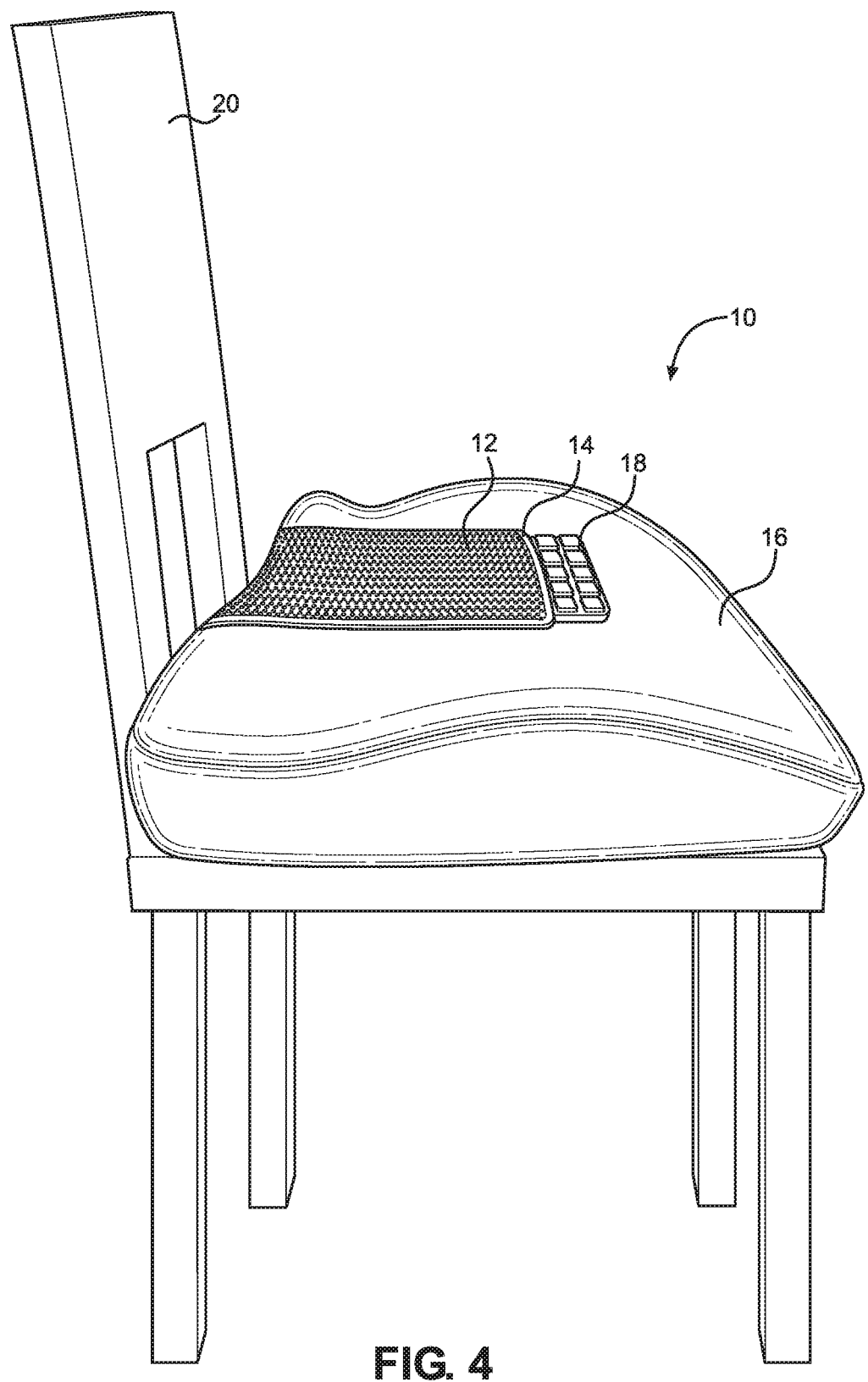
FIG. 4 is a side perspective view of an exemplary embodiment of the present invention, shown positioned on a seat.

Referring to FIGS. 1 through 4, the present invention may include a sitting cushion integrating heating and cooling elements and adapted in shape to relieve tailbone and hemorrhoid pain. The uniquely adapted treatment seat integrates hot or cold pads into a sitting cushion for providing significant enhanced pain relief and comfort. Thereby, the present invention "solves the problem" of providing both a comfortable surface to sit on while applying heat or cold to relieve lower back, tailbone and hemorrhoid discomfort.

It should be understood by those skilled in the art that the use of directional terms such as upper, lower, upward, downwardly, top, left, right and the like are used in relation to the illustrative embodiments as they are depicted in the figures, the upward direction (or upper) being toward the top of the corresponding figures, downward direction being toward the bottom of the corresponding figures.

The present invention includes a seat portion 10 providing a storage space 12 for removably retaining heating-cooling elements 18. The seat portion 10 may be a sitting cushion having a uniquely shaped operative contoured surface 16. The storage space 12 may be a mesh pocket applied to cushion sewed or adhered using adhesive material sitting cushion. The heating-cooling elements 18 may be gel pad which can be cooled in freezer and/or heated in a microwave and slid into an opening 14 of the pocket/compartment 12.

A method of manufacturing the present invention may include, the following. A manufacturer may first cut the mesh pocket in a size and shape to assure coverage of the affected areas designed to be treated by the apparatus, mainly the tailbone, lower back and external hemorrhoid (peri-anal) regions. This area can vary in size and shape as long as it provides coverage for the affected regions. The mesh pocket may be attached to the sitting cushion by way of sewing or any chemical adhesion method. A gel pad may be used which will fit into the mesh pocket and be large enough to provide coverage for the affected area. The gel pad may be either heated or cooled and subsequently to being placed into the mesh pocket.

The manufacturer may start from a generic sitting cushion, attach the mesh pocket to the sitting cushion and place a gel pad which has been heated in a microwave (or other generic heating apparatus) or cooled in the freezer (or other cooling apparatus).

The pocket and pad must be measured to provide coverage to the tailbone, lower back and perianal (hemorrhoid) region. The contours the operative contoured surface 16 are dimensioned and adapted so that when the user arrives at the appropriate size, the pocket 12 and temperature element 18 are cut to the appropriate size and the pocket (or electrical stimulation pad) is attached to the sitting cushion 10 using adhesives or stitching. The back of the operative contoured surface 16 may have a slight raised area to able to rest the lower back while helping to provide a guide so that the subject is correctly positioned on the operative contoured surface 16 of the cushion 10. A lateral contour may raise posterior thigh allowing buttocks and specifically lower spine and external hemorrhoids vessels to be in direct contact with the heating-cooling element 18. The lateral contour may achieve a maximum elevation (relative to the bottom surface) approximately eight inches from the rear of the seat portion 10 and then slope continuously downward in a forward direction. As a result, the seat portion 10 may provide an elevated posterior thigh causing flexion at the hip, when the present invention is placed on a seat 20 with the operative contoured surface 16 upward-facing.

In one embodiment, the operative contoured surface 16 provides an angled support surface (due to the angle of inclination of the surfaces) including a pair of spaced apart thigh contours 30 defining an anorectal portion 40 dimensioned and adapted accommodate a human sitters anorectal/ anus when seated on the operative contoured surface 16. Thigh contours 30 are concave shapes configured to spread the sitter's thighs so as to evenly distribute pressure from the anorectal portion 40 onto the anorectal/anus of the sitter. The anorectal portion 40 is where the heating-cooling element 18 is disposed so as to be urged against the 'spread' anus of the sitter.

The temperature adaptive element may be a "hot or cold" gel insert. Heat is better for enhanced relaxation and increased circulation related to anorectal disorders associated with muscle spasm, anal fissures as an example as well as external thrombotic hemorrhoids since the heat will help to dissolve the clots. Cold as discussed elsewhere, aids in reducing inflammation and works best to alleviate pain.

In an alternative embodiment 22, other elements which could be beneficial would be to attach an electrical stimulation device to the area currently designed to contain the mesh pocket and gel pad. Attaching an electrical stimulation device to a sitting cushion (in the area currently designed to contain the mesh pocket and gel pad) would also allow relief of low back, tailbone and hemorrhoid pain and discomfort. The apparatus would differ by applying an electrical stimulation pad instead of a pocketed gel pad—i.e., relief would be accomplished by using muscle stimulation verses temperature-initiated relief based on cold (anesthesia and anti-inflammatory) or heat (soothing and improved circulatory response). Additionally, the integrated element 24 of the alternative embodiment 22 could be integrated along the operative contoured surface 16 of the therapeutic cushion 10.

While the invention has been illustrated and described with respect to specific illustrative embodiments and modes of practice, it will be apparent to those skilled in the art that various modifications and improvements may be made without departing from the scope and spirit of the invention. Accordingly, the invention is not to be limited by the illustrative embodiments and modes of practice.

Said mixtures and combinations thereof, most likely will require at least one topical carrier selected from the group consisting of creams, ointments, gel, lotions, foam and mixtures and combinations thereof, wherein said composition is designed for internal and or external topical use and application, and said composition is designed to relieve one or all of the following: swelling, burning, pain and itching, irritation, inflammation, protrusion as well as protect inflamed and or irritated tissues, or provide a cooling sensation to the various signs and symptoms caused by various disorders afflicting the anus and rectum.

It should be understood, of course, that the foregoing relates to exemplary embodiments of the invention and that modifications may be made without departing from the spirit and scope of the invention as set forth in the following claims.

What is claimed is:

1. A seat comprising:
    an operative surface dimensioned to accommodate a human sitter, wherein the operative surface has a perimeter defined by a front edge, a rear edge and two opposing longitudinal edges, wherein the operative surface defines a plurality of longitudinal contours extending between the rear edge and the front edge;
    each longitudinal contour comprising:
        a first elevation along the rear edge; and
        a second elevation approximately eight inches from the rear edge, wherein the second elevation is a maximum elevation for the operative surface, wherein the plurality of longitudinal contours defines a latitudinal concave portion having maximum elevations at each of two opposing longitudinal thigh contours;
    wherein the operative surface defines a plurality of latitudinal contours extending between the two opposing longitudinal edges, wherein the plurality of latitudinal contours defines a centrally disposed longitudinal concave portion;
    an anorectal area of the operative surface, the anorectal area defined by the longitudinal concave portion between the first and second elevations, wherein the latitudinal and longitudinal concave portions are oriented perpendicular relative to each other so that the two opposing longitudinal thigh contours are configured to spread both thighs, respectively, of said human sitter while the latitudinal concave portion causes flexion of both hips of said human sitter simultaneously with said thigh spreading.

2. The seat of claim 1, wherein the second elevation of each longitudinal contour is configured to urge a posterior thigh of the human sitter, causing flexion at an associated hip of the human sitter,
    whereby the spread of both thighs and flexion of said hips of said human sitter urges the anorectal area against the spread anus of the human user.

3. The seat of claim 1, further comprising:
    a pocket disposed along the anorectal area; and
    a temperature-adapted element retained in the pocket.

4. The seat of claim 1, further comprising:
    a temperature-adapted element integrated to the anorectal area.

5. A method of treating anorectal disorders, comprising:
    administering a composition to an anorectal region of a human user; and
    sitting the human user on the seat of claim 1,
    whereby the two opposing longitudinal thigh contours spread both posterior thighs of the human user allowing associated buttocks and external hemorrhoids vessels to be in direct contact with the anorectal area.

* * * * *